US012191004B2

United States Patent
Mukherjee et al.

(10) Patent No.: US 12,191,004 B2
(45) Date of Patent: Jan. 7, 2025

(54) MACHINE LEARNING SYSTEM WITH TWO ENCODER TOWERS FOR SEMANTIC MATCHING

(71) Applicant: MICROSOFT TECHNOLOGY LICENSING, LLC, Redmond, WA (US)

(72) Inventors: Sudipto Mukherjee, Seattle, WA (US); Liang Du, Redmond, WA (US); Ke Jiang, Bellevue, WA (US); Robin Abraham, Redmond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 366 days.

(21) Appl. No.: 17/850,763

(22) Filed: Jun. 27, 2022

(65) Prior Publication Data

US 2023/0420085 A1     Dec. 28, 2023

(51) Int. Cl.
| | | |
|---|---|---|
| *G16C 20/70* | (2019.01) | |
| *G06N 3/04* | (2023.01) | |
| *G16C 20/10* | (2019.01) | |

(52) U.S. Cl.
CPC ............ *G16C 20/70* (2019.02); *G06N 3/04* (2013.01); *G16C 20/10* (2019.02)

(58) Field of Classification Search
CPC ........ G16C 20/70; G16C 20/10; G16C 20/40; G06N 3/04; G06N 3/045; G06N 3/0895
See application file for complete search history.

(56) References Cited

U.S. PATENT DOCUMENTS

| | | |
|---|---|---|
| 4,591,948 A | 5/1986 | Sato et al. |
| 4,922,052 A | 5/1990 | Shimizu et al. |
| 4,944,848 A | 7/1990 | Kaufhold |
| (Continued) | | |

OTHER PUBLICATIONS

"Formulation Examples", Retrieved from: https://web.archive.org/web/20210518173423/https://www.jrspharma.com/pharma_en/resources/formulation-examples/, May 18, 2021, 3 Pages.

(Continued)

*Primary Examiner* — Mohammad K Islam
(74) *Attorney, Agent, or Firm* — Benjamin Keim; Newport IP, LLC

(57) ABSTRACT

This disclosure describes a machine learning system that includes a contrastive learning based two-tower model for retrieval of relevant chemical reaction procedures given a query chemical reaction. The two-tower model uses attention-based transformers and neural networks to convert tokenized representations of chemical reactions and chemical reaction procedures to embeddings in a shared embedding space. Each tower can include a transformer network, a pooling layer, a normalization layer, and a neural network. The model is trained with labeled data pairs that include a chemical reaction and the text of a chemical reaction procedure for that chemical reaction. New queries can locate chemical reaction procedures for performing a given chemical reaction as well as procedures for similar chemical reactions. The architecture and training of the model make it possible to perform semantic matching based on chemical structures. The model is highly accurate providing an average recall at K=5 of 95.9%.

20 Claims, 7 Drawing Sheets

(56) References Cited

U.S. PATENT DOCUMENTS

| | | | |
|---|---|---|---|
| 5,082,358 | A | 1/1992 | Tabata et al. |
| 5,221,721 | A | 6/1993 | Selvig |
| 7,115,589 | B2 | 10/2006 | Weigele et al. |
| 7,148,245 | B2 | 12/2006 | Bernardon et al. |
| 7,435,837 | B2 | 10/2008 | Gross et al. |
| 7,991,730 | B2 | 8/2011 | Wagner et al. |
| 8,299,267 | B2 | 10/2012 | Ghosh et al. |
| 8,926,998 | B2 | 1/2015 | Hedrick et al. |
| 8,927,117 | B2 | 1/2015 | Buesing et al. |
| 8,927,281 | B2 | 1/2015 | Boitano et al. |
| 2022/0270711 | A1* | 8/2022 | Feala .................. G16B 45/00 |
| 2023/0410950 | A1* | 12/2023 | Godin ................. G06N 3/08 |
| 2024/0135172 | A1* | 4/2024 | Hyuga ............... G06T 7/0004 |

OTHER PUBLICATIONS

Beltagy, et al., "SciBERT: A Pretrained Language Model for Scientific Text", In Repository of arXiv:1903.10676v3, Sep. 10, 2019, 6 Pages.

Chithrananda, et al., "ChemBERTa: Large-Scale Self-Supervised Pretraining for Molecular Property Prediction", In Repository of arXiv:2010.09885v2, Oct. 23, 2020, 7 Pages.

Devlin, et al., "BERT: Pre-training of Deep Bidirectional Transformers for Language Understanding", In Repository of arXiv:1810.04805v2, May 24, 2019, 16 Pages.

Finelli, Luca, "The Art of Drug Design in a Technological Age", Retrieved from: https://www.novartis.com/stories/art-drug-design-technological-age?utm_source=LT, Nov. 18, 2021, 5 Pages.

Guo, et al., "MM-Deacon: Multimodal Molecular Domain Embedding Analysis via Contrastive Learning", In Proceedings of the 60th Annual Meeting of the Association for Computational Linguistics, May 22, 2022, 21 Pages.

Lowe, Daniel, "Chemical Reactions from US Patents (1976-Sep. 2016)", Retrieved from: https://figshare.com/articles/dataset/Chemical_reactions_from_US_patents_1976-Sep2016_/5104873, Jun. 13, 2017, 1 Page.

Rajan, et al., "DECIMER: Towards Deep Learning for Chemical Image Recognition", In Journal of Cheminformatics, vol. 12, Article 65, Oct. 27, 2020, 9 Pages.

Rajan, et al., "STOUT: SMILES to IUPAC Names using Neural Machine Translation", In Journal of Cheminformatics, vol. 13, Article 34, Apr. 27, 2021, 14 Pages.

Vaswani, et al., "Attention Is All You Need", In Repository of arXiv:1706.03762v5, Dec. 6, 2017, 15 Pages.

Guo, et al., "MM-Deacon: Multimodal molecular domain embedding analysis via contrastive learning", Retrieved From: https://www.biorxiv.org/content/10.1101/2021.09.17.460864v1.full.pdf, Sep. 20, 2021, 21 Pages.

Guo, et al., "Multilingual Molecular Representation Learning via Contrastive Pre-training", In repository of arXiv:2109.08830v3, Apr. 18, 2022, 13 Pages.

"International Search Report and Written Opinion Issued in PCT Application No. PCT/US23/022629", Mailed Date: Sep. 13, 2023, 12 Pages.

Schwaller, et al., "Mapping the Space of Chemical Reactions Using Attention-Based Neural Networks", In repository of arxiv:2012.06051v1, Dec. 9, 2020, 36 Pages.

* cited by examiner

104

CHEMICAL REACTION SKETCH

O=C([O-])[O-].[Na+].[Na+].O.C1CCOC1.CCOC(=O)Cl.NC(CO)CO>CCOC(=O)NC(CO)CO

MACHINE LEARNING SYSTEM
100

102

CANDIDATE CHEMICAL REACTION PROCEDURES

| DOCUMENT ID 108 | CHEMICAL REACTION PROCEDURE 106 | SIMILARITY SCORE 110 |
| --- | --- | --- |
| 3813B2 | 1-Propylimidzole and 3-chloro-1,2-propendiole were stirred at 130°C... | 0.8501 |
| 5914A1 | 1-Butylimidazole and 3-chloro-1,2-propendiol were stirred for 48h, after which... | 0.8451 |
| 0843Z9 | 1-Ethylimidazole and 3-chloro-1,2-propendiol were stirred in a flask placed under vacuum... | 0.8353 |

MACHINE LEARNING SYSTEM WITH TWO ENCODER TOWERS FOR SEMANTIC MATCHING

BACKGROUND

Chemical reactions are studied in multiple domains such as drug discovery, catalysis, chemical manufacturing processes, and energy and fuel production. Oftentimes even if the reactants and products are known, significant experimentation and effort are needed to develop a process for converting the reactants to the products. There are also many chemical reactions that can be performed by multiple alternative processes which provide the same outcome. Thus, there is often a significant gap between knowledge of a chemical reaction and knowledge of the process to perform that reaction.

However, there exists a wealth of knowledge about processes for chemical reactions in research publications, patents, regulatory filings, and internal documents within enterprises. Chemists can search existing documents to understand possible preparation processes for a desired product. Yet, prior techniques suffer from the inability to accurately search the chemical literature beyond identifying exact matches. The same chemical entity may be described by entirely different text strings (e.g., "sodium hydride" and "NaH") as well as non-textually by a diagram of a molecular structure. Even attempts to create standardized nomenclature such as preferred IUPAC (International Union of Pure and Applied Chemistry) names use complex sets of rules that can result in multiple possible names for a single chemical entity. Unfortunately, much of the existing knowledge about chemical reaction procedures is unusable because it cannot be effectively and efficiently searched.

It would be of great value to chemists and others to be able to fetch textual procedures of chemical reactions based on information about the chemical reaction without the limitations of exact keyword matching. The following disclosure is made with respect to these and other considerations.

SUMMARY

This disclosure describes a machine learning system that trains a two-tower model with contrastive learning for retrieval of relevant chemical reaction procedures given a query chemical reaction sketch. This machine learning system includes joint representation of chemical reaction sketches and chemical reaction procedures as real-valued vectors. Candidate chemical reaction procedures are retrieved by semantic matching that accurately identifies the same or similar chemical entities with similar backbone structures even with different positions of functional groups. This technique creates a machine learning system that can derive understanding of functional groups, how carbon backbone structures modify in a reaction, and exchange of functional groups between reactant(s) and product(s). It is also able to associate various forms of names (e.g., chemical formulas, common names, and abbreviations) with a chemical structure and perform semantic matching across a variety of different naming formats.

The two-tower model uses a reaction encoder and a procedure encoder that both use attention-based transformer models. The reaction encoder processes a tokenized representation of a chemical reaction sketch to generate a reaction embedding which can be a real-valued vector. A chemical reaction sketch is all or part of a chemical reaction including only products, only reactants, or only a single chemical entity. The procedure encoder processes a tokenized representation of a chemical reaction procedure to generate a procedure embedding which can be a real-valued vector. A chemical reaction procedure is a textual description of how a chemical reaction is carried out in a laboratory or industrial plant setting. A chemical reaction procedure may include any of reagents, catalysts, and solvents as well as temperature, pressure, yield percentages of the product(s), and operating conditions of the reaction as well as additional information.

Each encoder may include a transformer network followed by a pooling layer, a normalization layer, and finally a fully connected neural network that generate the respective reaction embeddings and procedure embeddings. The reaction embeddings and procedure embeddings are mapped to a joint embedding space in which semantically similar inputs are mapped to similar locations. A single layer of the transformer network may include a multi-head attention layer and at least one fully connected feed-forward layer. The pooling layers may be implemented as max poolers and generate a high-dimensional vector (e.g., 256 or 512) from the output of the transformer network. The normalization layers normalize the high-dimensional vectors from the pooling layers. The neural networks may be implemented as fully connected, feed-forward, multilayer neural networks.

The two encoders are trained with labeled data pairs that each includes a chemical reaction procedure labeled with a representation of the chemical reaction described in that chemical reaction procedure. The chemical reaction may be represented in any number of different ways including by use of Simplified Molecular-Input Line-Entry System (SMILES) notation. The chemical reaction is provided to the reaction encoder and the chemical reaction procedure is provided to the procedure encoder. The machine learning model is trained using contrastive learning objective so that the correct chemical reaction has maximum similarity with the corresponding chemical reaction procedure in the joint embedding space. Thus, training can be performed to minimize a loss function between a reaction embedding and a procedure embedding corresponding to a labeled data pair.

Once properly trained, the machine learning model can be used to identify one or more chemical reaction procedures from a corpus of chemical reaction procedures in response to receiving a chemical reaction sketch from a user. The chemical reaction sketch is tokenized and the reaction token sequence is provided to the reaction encoder that generates a reaction embedding. Similarity between this reaction embedding and multiple procedure embeddings (corresponding to the chemical reaction procedures in the corpus) in a shared embedding space are determined. A number of candidate chemical reaction procedures (e.g., 5) that have the highest similarity are returned as the output.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. The figures are schematic representations and items shown in the figures are not necessarily to scale.

FIG. 1 is an overview of a machine learning system that provides candidate chemical reaction procedures in response to a chemical reaction sketch submitted as a query.

DETAILED DESCRIPTION

Figure 2:
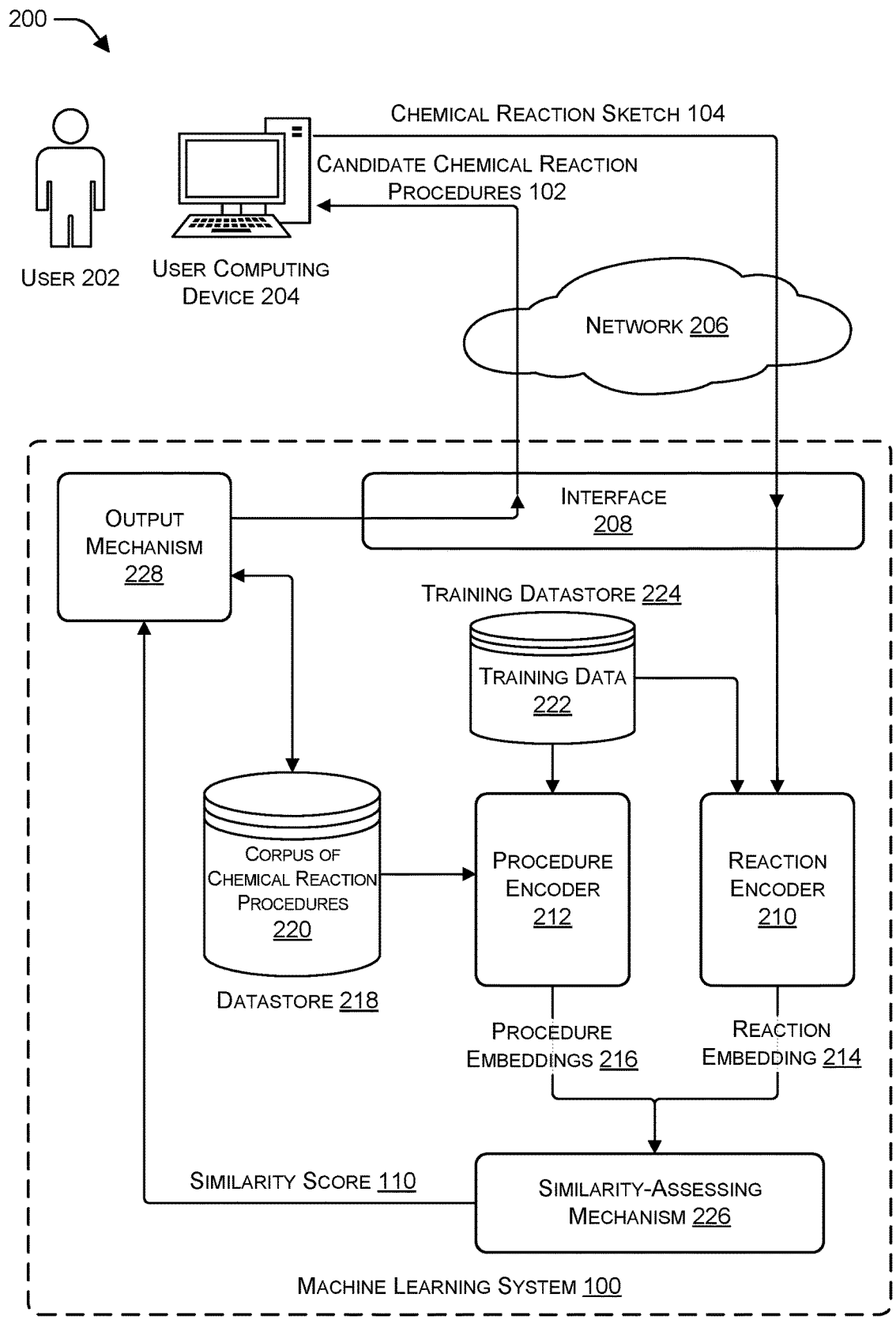
FIG. 2 is an illustrative architecture of the machine learning system shown in FIG. 1.

This disclosure provides a novel system and technique using machine learning for identifying relevant chemical reaction procedures from a query consisting of all or part of a chemical reaction. This system and technique can identify exact matches if a procedure for the queried chemical reaction exists in the set of documents being searched. It also can find similar (and thus chemically relevant) procedures for new chemical reactions that do not exactly match any of the chemical reaction procedures available to the system. This flexible and accurate technique allows users to readily identify a textual description of a chemical reaction procedure to study the reaction and context in greater detail. It can also identify alternate reactions that generate the same products. This effective searching and retrieval system makes it possible to explore opportunities for optimizations of chemical reactions that may lower cost, improve selectivity, and decrease non-desirable byproducts such as hazardous or toxic byproducts.

FIG. 1 shows a machine learning system 100 that provides candidate chemical reaction procedures 102 in response to a chemical reaction sketch 104 submitted as a query. The chemical reaction sketch 104 is provided by a user, such as a chemist, as a search query. A chemical reaction sketch 104 is a representation of all or part of a chemical reaction. The chemical reaction sketch 104 may include reactants and products, only reactants, or only products. A single chemical entity, either designated as reactant or product or without designation, may also be a chemical reaction sketch 104. Thus, a chemical reaction sketch 104 includes everything from a single chemical entity to a full reaction specifying all reactants and products. This provides the user who may have an initial idea about potential starting reactants and potential main product flexibility in providing the query based on available information and allows for identification of related chemical reaction procedures when partial information is provided.

The chemical reaction sketch 104 may be represented in any number of ways or techniques for specifying chemical entities and chemical reactions. In one implementation, the chemical reaction sketch 104 is provided using SMILES strings. SMILES is a specification in the form of a line notation for describing the structure of chemical species using short ASCII strings. Specific instances can be called SMILES strings. SMILES and techniques for generating canonicalizations using SMILES are known to those of ordinary skill in the art. See Weininger D., "*SMILES, a chemical language and information system. 1. Introduction to methodology and encoding rules*". Journal of Chemical Information and Computer Sciences. 28 (1): 31-6. (February 1988).

In one implementation, the chemical reaction sketch 104 is provided using the International Chemical Identifier (InChI). InChI is a textual identifier for chemical substances, designed to provide a standard way to encode molecular information. The identifiers describe chemical substances in terms of layers of information—the atoms and their bond connectivity, tautomeric information, isotope information, stereochemistry, and electronic charge information. They can express more information than the simpler SMILES notation and differ in that every structure has a unique InChI string. InChI and techniques for generating representations of chemical entities using InChI are known to those of ordinary skill in the art. See Heller, S. et al., I. "*InChI—the worldwide chemical structure identifier standard*". Journal of Cheminformatics. 5 (1): 7, (2013).

In one implementation, the chemical reaction sketch 104 is provided using International Union of Pure and Applied Chemistry (IUPAC) names such as preferred IUPAC names. An IUPAC name is a systematic name that meets the recommended IUPAC rules. In chemical nomenclature, a preferred IUPAC name (PIN) is a unique name, assigned to a chemical substance and preferred among the possible names generated by IUPAC nomenclature. The "preferred IUPAC nomenclature" provides a set of rules for choosing between multiple possibilities in situations where it is important to decide on a unique name. Persons of ordinary skill in the art will know how to identify and name chemical entities using IUPAC names. See *Nomenclature of Organic Chemistry: IUPAC Recommendations and Preferred Names* 2013 (*Blue Book*). Cambridge: The Royal Society of Chemistry. 2014.

In one implementation, the chemical reaction sketch 104 is provided with a graphical representation or schematic of the molecular structure. The graphical representation can be converted to another representation such as SMILEs using tools and techniques known to those of ordinary skill in the art such as Mathpix© (available at mathpix.com) or DECIMER (Raj an, K. et al., DECIMER: towards deep learning for chemical image recognition. *J Cheminform* 12, 65 (2020). Alternatively, if the machine learning system 100 is trained using graphical representations or schematics they can be provided directly without translation or conversion.

In one implementation, the chemical reaction sketch 104 is provided using common names or trade names. Common names or trade names may be converted to another format such as IUPAC names or SMILES strings by reference to a lookup table or by using other known techniques for converting between different representations of chemical entities.

The chemical reaction sketch 104 is provided to a machine learning system 100. The machine learning system 100 compares the chemical reaction sketch 104 to a set of documents that contain textual descriptions of chemical reaction procedures and identifies candidate chemical reaction procedures 102 from the set of documents. The search space may contain hundreds of thousands or millions of documents.

The chemical reaction sketch 104 is mapped by the machine learning system 100 to an embedding space of similar chemical families so that relevant chemical reaction procedures can be retrieved. The machine learning system 100 has an implicit understanding of the functional groups in chemical compounds, reaction properties of diverse carbon backbone structures as well as an ability to group similar backbone structures. The machine learning system 100 relates these properties of chemical reactions to the corresponding procedure texts in a joint embedding space, thereby enabling such search and retrieval operations from chemical reaction sketches 104.

The machine learning system 100 includes a contrastive learning based two-tower model for retrieval of relevant chemical reaction procedures when queried with a chemical reaction sketch 104. The machine learning system 100 is based on joint representation of chemical reaction sketches and chemical reaction procedures as real-valued vectors generated by two transformer models—one for each data modality. Further details of the machine learning system 100 are provided below.

The machine learning system 100 outputs candidate chemical reaction procedures 102 which include one or more specific chemical reaction procedures 106. A chemical reaction procedure 106 is a detailed description of how a chemical reaction is carried out in a laboratory or industrial plant starting with the required reagents, catalysts, and solvents. A chemical reaction procedure 106 may include the temperature, pressure, and operating conditions of the reaction, the amounts of chemicals to be added, and actions to be performed such as stirring, heating, or filtering. It may also include proportionate yields of the final product(s). The machine learning system 100 may output one or more chemical reaction procedures 106 that are most similar to the query. Similarity is identified by the closeness of vectors representing the chemical reaction sketch 104 and the chemical reaction procedures 106. The candidate chemical reaction procedures 102 may be provided in any format such as the illustrative table shown in FIG. 1.

In some implementations, the chemical reaction procedures 106 are passages from larger documents (e.g., patents or scientific publications). A chemical reaction procedure 106 may be provided together with a document identifier (ID) 108 of the document in which the chemical reaction procedure 106 is found. The document ID 108 is any identifier such as a patent number or citation that uniquely identifies the document. The documents provide context for the chemical reaction procedures 106 and may additionally be provided by the machine learning system 100. However, the candidate chemical reaction procedures 102 may also be provided without document IDs 108.

A similarity score 110 determined by the machine learning system 100 may be included in the candidate chemical reaction procedures 102. The similarity score 110 indicates how close the machine learning system 100 deems the chemical reaction procedure 106 to match the chemical reaction sketch 104. The "best" match as subjectively identified by the user may not necessarily be the chemical reaction procedure 106 with the highest similarity score 110. Thus, in some implementations, the machine learning system 100 will return candidate chemical reaction procedures 102 that include more than just the chemical reaction procedure 106 with a highest similarity score 110. However, the similarity score 110 may also be omitted from the candidate chemical reaction procedures 102 returned to the user. The chemical reaction procedures 106 included in the candidate chemical reaction procedures 102 may be ranked or ordered according to similarity score 110 whether or not the similarity score 110 is displayed to a user.

FIG. 2 shows an illustrative architecture 200 of the machine learning system 100 introduced in FIG. 1. In the illustrated implementation, the machine learning system 100 is implemented as a cloud-based system that is physically remote from the user 202 and the user computing device 204 used for submitting the chemical reaction sketch 104. In this implementation, data is transferred between the user computing device 204 and the machine learning system 100 via a network 206. The network 206 may be any type of communications network(s) for transferring data between two computing devices such as the Internet. In another implementation, the machine learning system 100 may be running locally on the user computing device 204. The machine learning system 100 may also be implemented in a distributed architecture with some components on the user computing device 204 and some components in the cloud. The machine learning system 100 also includes one or more processors and one or more memories (not shown) to implement the functionality of other components of the machine learning system 100.

The chemical reaction sketch 104 as described in FIG. 1 may be transmitted via the network 206 to an interface 208 in the machine learning system 100. The interface 208 is configured to receive a given chemical reaction sketch 104 from the user computing device 204 (and/or from any other source). The interface 208 also formulates and transmits candidate chemical reaction procedures 102 to the user computing device 204. The interface 208 itself may correspond to a frontend software layer that the machine learning system 100 uses to interact with the user 202.

Figure 3:
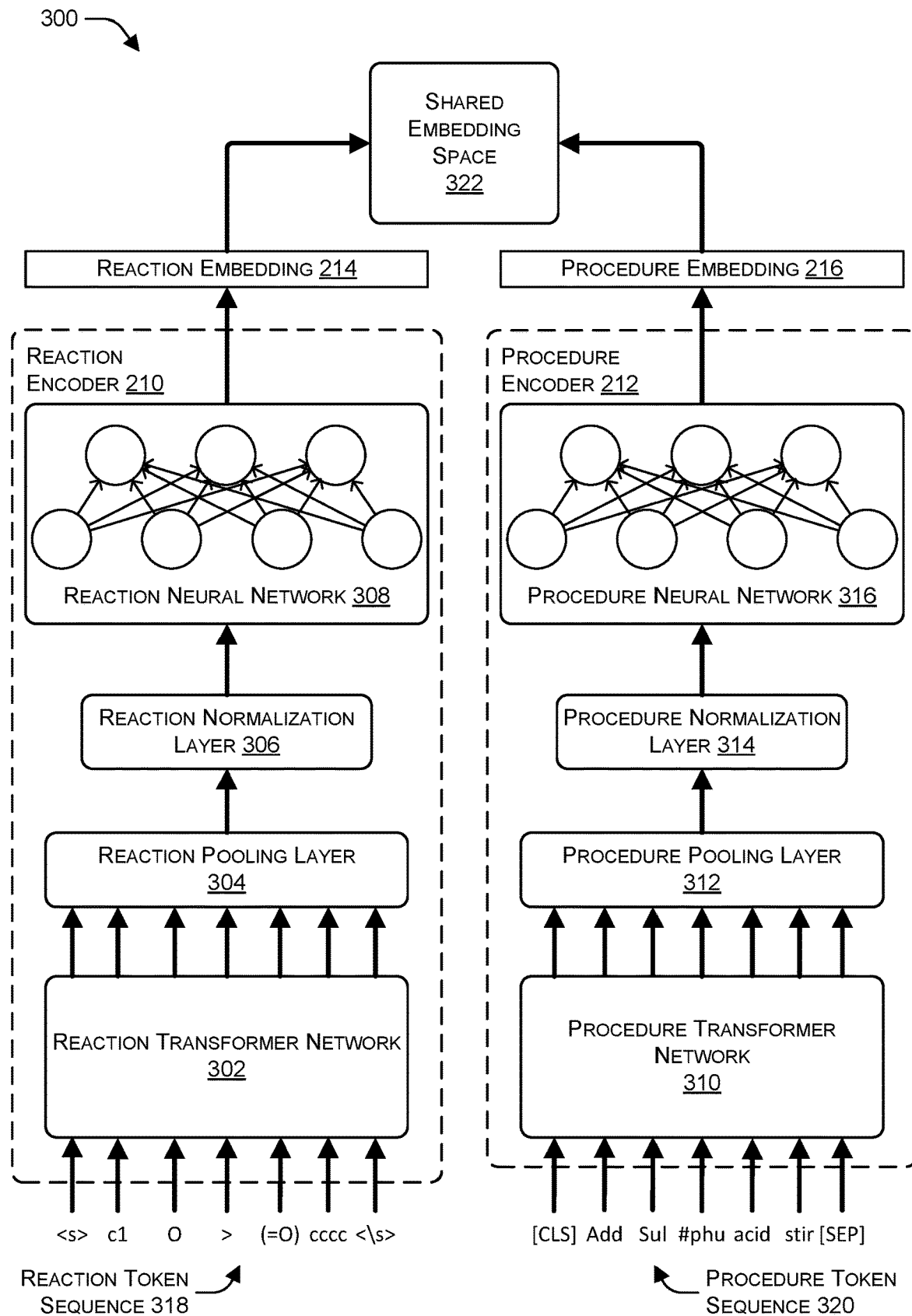
FIG. 3 is an illustrative diagram of two encoder towers used for semantic matching between chemical reaction sketches and chemical reaction procedures.

The machine learning system 100 includes a reaction encoder 210 and a procedure encoder 212. The reaction encoder 210 and the procedure encoder 212 represent the two towers of a contrastive learning based two-tower model. Further details of the reaction encoder 210 and the procedure encoder 212 are shown in FIG. 3.

The reaction encoder 210 receives the chemical reaction sketch 104. The chemical reaction sketch 104 may be tokenized before it is provided to the reaction encoder 210. The reaction encoder 210 is configured to create a reaction embedding 214 of the chemical reaction sketch 104. The reaction embedding 214 represents the chemical reaction sketch 104 in a high-dimensional space.

The procedure encoder 212 is similarly configured to create procedure embeddings 216 of the chemical reaction procedures 106 in a high-dimensional space. The reaction embedding 214 and the procedure embeddings 216 are placed in a shared embedding space. A datastore 218 containing a corpus of chemical reaction procedures 220 is the source of the chemical reaction procedures 106 provided to the procedure encoder 212. The chemical reaction procedures 106 may come from preexisting documents that are public such as patent or scientific publications or proprietary documents such as internal documents of an enterprise. In some implementations, the datastore 218 may be located outside of the machine learning system 100. The corpus of chemical reaction procedures 220 may contain hundreds of thousands, millions, or more chemical reaction procedures 106. Thus, the procedure encoder 212 may generate a procedure embedding 216 in the shared embedding space for each of the chemical reaction procedures 106 in the corpus 220.

Before being used to identify relevant chemical reaction procedures 106, the reaction encoder 210 and the procedure encoder 212 of the machine learning system 100 are trained with labeled pair-wise data through contrastive learning. Training enables the encoders to learn the weights for generating the reaction embeddings 214 and the procedure embeddings 216. Training data 222 is accessed from a training datastore 224. Some or all of the corpus of chemical reaction procedures 220 may be used as the training data 222. The training data 222 are pairs of training chemical reaction procedures and training representations of chemical reactions. The training data 222 may be split into training, development, and test splits. The development split is used to select hyperparameters for the model. The training split is used to train the weights of the model. The test split is used to test the accuracy of the model.

The training chemical reaction procedures describe procedures for performing the respective paired training chemical reactions. In an implementation, the training representations of chemical reactions include complete reactions with all reactants and products. The chemical reactions included in the training data 222 may be represented, for example, as SMILES strings. The chemical reaction sketches 104 are provided to the reaction encoder 210 in the same format as the chemical reactions in the training data 222 used to train the reaction encoder 210. If the user computing device 204 provides a chemical reaction sketch 104 in a different format, the chemical reaction sketch 104 is converted by the interface 208. Alternatively, the machine learning system 100 may include multiple reaction encoders (not shown) each trained on a different representation of chemical reactions (e.g., one for SMILES, one for InChI, and one for IUPAC names). The interface 208 may identify the format of the chemical reaction sketch 104 and route the input to the reaction encoder trained on that format of chemical reactions.

During training, a chemical reaction procedure from the training data 222 is provided to the procedure encoder 212 and the paired chemical reaction is provided to the reaction encoder 210. The training data 222 (both the chemical reaction procedures and the chemical reactions) may be cleaned before being used for training. Before training, one or both of the reaction encoder 210 and the procedure encoder 212 may be initialized with weights from other machine learning models. For example, the reaction encoder 210 may be initialized with weights developed from a machine learning model configured to convert between a first representation of a chemical entity and a second representation of the chemical entity. One example of such a model is provided in Guo, Z., et al., *MM-Deacon: Multimodal molecular domain embedding analysis via contrastive learning*, bioRxiv 2021.09.17.460864; Posted Sep. 20, 2022, which provides a technique from converting from SMILES to IUPAC names. The procedure encoder 212, for example, may be initialized with weights from a BERT-based language model of scientific publications. One example of this type of model is provided in Beltagy, I. et al., SCIBERT: A Pretrained Language Model for Scientific Text, Proceedings of the Conference on Empirical Methods in Natural Language Processing (EMNLP 2019). Although these different models are designed for solving different problems, initialization may reduce training time. However, initialization before training is optional and may be omitted. The training maximizes the similarity in the shared embedding space between the procedure embedding 216 and a reaction embedding 214 corresponding to each chemical reaction procedure-chemical reaction pair from the training data 222.

Following training, similarity between the reaction embedding 214 generated from the chemical reaction sketch 104 and procedure embeddings 216 generated from chemical reaction procedures 106 in the datastore 218 is determined by a similarity-assessing mechanism 226. The similarity-assessing mechanism 226 is configured to determine a similarity by comparing a reaction embedding 214 with a procedure embedding 216. The similarity-assessing mechanism 226 computes a single similarity score 110 for each compared pair of embeddings. The similarity score 110 may be a number that varies from 0 representing no similarity to 1 representing a perfect match. In one implementation, the similarity-assessing mechanism 226 determines a cosine similarity between a reaction embedding 214 and a procedure embedding 216. Cosine similarity is the cosine of the angle between two vectors in an inner product space, that is, the dot product of the vectors divided by the product of their lengths. Cosine similarity does not depend on the magnitudes of the vectors, but only on their angle. For example, two proportional vectors have a cosine similarity of 1 and two orthogonal vectors have a similarity of 0. An alternative technique for determining similarity that may be implemented by the similarity-assessing mechanism 226 is through negative Euclidean distance. The Euclidean distance between two vectors, such as a reaction embedding 214 and a procedure embedding 216, is defined as the smallest distance between any two points from the two vectors. Lower Euclidean distance indicates higher similarity.

Due to the training, the procedure embeddings 216 closest in the shared embedding space to the reaction embedding 214 will correspond to the chemical reaction procedures 106 that are most relevant to the chemical reaction sketch 104. The similarity score 110 generated by the similarity-assessing mechanism 226 represents the relevance or closeness of a match between the chemical reaction sketch 104 and the chemical reaction procedures 106. The similarity scores 110 are provided to an output mechanism 228.

The output mechanism 228 may identify a predetermined number of chemical reaction procedures 106 (e.g., 5 or 10) that have the highest similarity out of all the chemical reaction procedures 106 in the datastore 218. The output mechanism 228 is further configured to provide this predetermined number of candidate chemical reaction procedures 102 to the interface 208. From the interface 208, the candidate chemical reaction procedures 102 are sent to the user computing device 204. The results provided by the output mechanism 228 may or may not include the similarity scores 110. The text of the chemical reaction procedures 106 may be obtained by the output mechanism 228 from the corpus of chemical reaction procedures 220 and included in the output generated from the output mechanism 228. The output mechanism 228 may function in conjunction with the interface 208 to format and present the candidate chemical reaction procedures 102 to the user computing device 204.

FIG. 3 shows a diagram 300 of two encoder towers used for semantic matching between chemical reaction sketches and chemical reaction procedures. The two encoder towers are the reaction encoder 210 and the procedure encoder 212 introduced in FIG. 2. The reaction encoder 210 and the procedure encoder 212 are illustrated as having parallel architectures. However, the architecture of each encoder may vary from the other by modifying one or more elements, omitting one or more elements, or including additional elements beyond those illustrated.

The reaction encoder 210 includes a reaction transformer network 302, a reaction pooling layer 304, a reaction normalization layer 306, and a reaction neural network 308. The procedure encoder 212 includes a procedure transformer network 310, a procedure pooling layer 312, a procedure normalization layer 314, and a procedure neural network 316. The reaction transformer network 302 takes as input a reaction token sequence 318 that is a tokenized representation of a chemical reaction sketch 104 (for queries) or a training chemical reaction (for training). The procedure transformer network 310 takes as input a procedure token sequence 320 that is a tokenized representation of a chemical reaction procedure 106 (for queries) or a training chemical reaction procedure (for training). The reaction token sequence 318 is mapped to a reaction token vector using a token embedding matrix and a position embedding function. Similarly, the procedure token sequence 320 is mapped to a procedure token vector using a token embedding matrix and a position embedding function. Thus, the reaction token sequence 318 and the procedure token sequence 320 may be provided to the respective transformer networks as the reaction token vector and the procedure token vector.

The reaction transformer network 302 comprises at least a multi-head attention layer and a fully-connected feed-forward layer configured to generate a reaction transformer output from the reaction token sequence 318. The reaction transformer network 302 is an attention-based model that attends to each token by making a representation of each token based on a weighted sum of representations of other tokens in the reaction token sequence 318. Thus, the tokens provided to the reaction transformer network 302 are converted into vectors, one for each token.

The reaction transformer network 302 may itself contain multiple layers such as between 2-12 layers or more cascaded on top of each other. Each layer within the reaction transformer network includes a multi-head attention layer and one or more fully-connected feed-forward layers. In one implementation, the reaction transformer network 302 contains six layers. In this implementation, the reaction transformer network 302 will include six multi-head attention layers each followed by at least one fully-connected feed-forward layer. Thus, the output of the fully-connected feed-forward layer will be the input to the next multi-head attention layer in the cascade. The number of layers in the reaction transformer network 302 may be varied to achieve a balance between speed and accuracy. Transformer networks are a specific type of neural network that includes at least one self-attention mechanism and at least one feed-forward neural network. Examples of transformers are provided in Devlin, et al., "*BERT: Pre-training of Deep Bidirectional Transformers for Language Understanding*," Proceedings of NAACL-HLT, 4171-4186 (2019), and Vaswani, et al., "Attention Is All You Need," Conference on Neural Information Processing Systems (NIPS 2017).

The reaction token sequence 318 is a string of tokens provided to the reaction transformer network 302. In one example, the chemical reaction sketch 104 is provided or converted to a SMILES string. The SMILES string is tokenized by separating the string into smaller meaningful elements called tokens. A start token (e.g., <s>) may be added to the start of the reaction token sequence 318 to indicate the start of the reaction. An end token (e.g., <\s>) may be added to the end of the reaction token sequence 318 to indicate the end of the reaction. Any type of suitable tokenization technique may be used such as a Byte-Pair Encoder (BPE) or regex-based tokenization. The number of tokens in the reaction token sequence 318 may be set to an upper maximum number such as 256 or 512. Sequences with more tokens may be truncated to the maximum length.

The procedure transformer network 310 may have a similar or identical architecture to the reaction transformer network 302. The procedure token sequence 320 is generated by any suitable tokenizer for converting a textual passage into a string of tokens. One suitable technique for tokenizing scientific texts is described in Beltagy, I. et al. The number of tokens in the procedure token sequence 320 may be set to an upper maximum number such as 256 or 512. Sequences with more tokens may be truncated to the maximum length. In an implementation, the same maximum number of tokens is set for both the reaction token sequence 318 and the procedure token sequence 320.

The reaction transformer output from the reaction transformer network 302 and the procedure transformer output from the procedure transformer network 310 are provided to the reaction pooling layer 304 and the procedure pooling layer 312 respectively. The reaction pooling layer 304 and the procedure pooling layer 312 may implement any type of pooling such as max pooling or average pooling. In some implementations, the reaction pooling layer 304 and the procedure pooling layer 312 may use different techniques. The reaction pooling layer 304 generates a high-dimensional vector from the reaction transformer output. The procedure pooling layer 312 generates a high-dimensional vector from the procedure transformer output. Thus, the multiple vectors output from each of the transformer networks are reduced to a single high-dimensional vector.

The high-dimensional vectors from the reaction pooling layer 304 and the procedure pooling layer 312 are provided to the reaction normalization layer 306 and the procedure normalization layer 314 respectively. The normalization layers normalize the high-dimensional vectors to create normalized vectors. Layer normalization ("LayerNorm") is a technique to normalize the distributions of intermediate layers. It enables smoother gradients, faster training, and better generalization accuracy. Without normalization, only the largest few features in the high-dimensional vectors will contribute to similarity. In one implementation, normalization subtracts the mean value across the dimensions in a vector and divides by the standard deviation to create new, normalized, values for each feature in the vector.

The normalized vector from the reaction normalization layer 306 is provided to the reaction neural network 308 and the normalized vector from the procedure normalization layer 314 is provided to the procedure neural network 316. In an implementation, the reaction neural network 308 and the procedure neural network 316 are fully connected neural networks. A fully connected neural network consists of a series of fully connected layers that connect every neuron in one layer to every neuron in the other layer. In an implementation, the reaction neural network 308 and the procedure neural network 316 are feed-forward neural networks. A feed-forward neural network is an artificial neural network in which the connections between nodes do not form a cycle. In an implementation, the reaction neural network 308 and the procedure neural network 316 are multi-layer neural networks (e.g., 2, 3, 4, 5, 6, or more) with at least one hidden layer. The reaction neural network 308 and the procedure neural network 316 may be implemented with any suitable activation function such as Rectified Linear Activation (ReLU), Logistic (Sigmoid), or Hyperbolic Tangent (Tanh). The activation functions of the reaction neural network 308 and the procedure neural network 316 may be non-linear.

The structure of the reaction neural network 308 and the procedure neural network 316 (e.g., number of layers, activation function) may be the same or different.

The output layer of the reaction neural network 308 is the reaction embedding 214. Similarly, the output layer of the procedure neural network 316 is the procedure embedding 216. Both the reaction embedding 214 and the procedure embedding 216 are represented as vectors such as real-valued vectors. The vectors may be high-dimensional vectors such as 256 or 512 dimensions and both vectors have the same number of dimensions.

Both the reaction embedding 214 and the procedure embedding 216 are embedded in a shared embedding space 322. This creates a joint embedding with inputs from both reaction token sequences 318 and procedure token sequences 320 in a common latent vector space that enables semantic association between chemical reactions (or sketches) and chemical reaction procedures.

Training with labeled pair-wise data minimizes a loss function between corresponding pairs of reaction embeddings 214 and procedure embeddings 216 from the training data 222. Training may be performed with contrastive loss and backpropagation to teach the machine learning system 100 to place paired embeddings close to each other in the shared embedding space 322. In one implementation, the loss function is InfoNCE loss. InfoNCE loss is a loss function for contrastive model training. It aims to estimate the mutual information between a pair of variables by discriminating between each positive pair and its associated K negative pairs. Other loss functions such as contrastive loss, triplet loss, N-pair loss, Noise Contrastive Estimation (NCE), and soft-nearest neighbors loss may also be used.

Illustrative Processes

Figure 4:
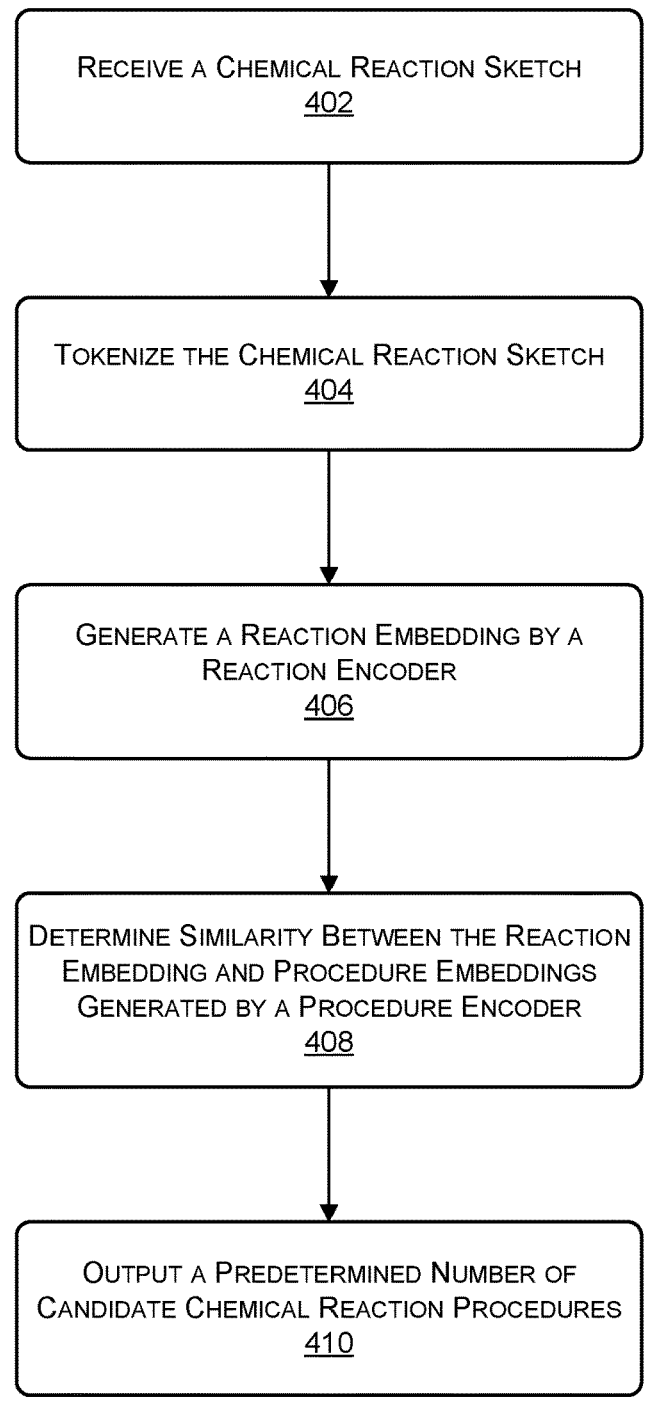
FIG. 4 is a flow diagram showing an illustrative process for outputting candidate chemical reaction procedures in response to a chemical reaction sketch.
Figure 5:
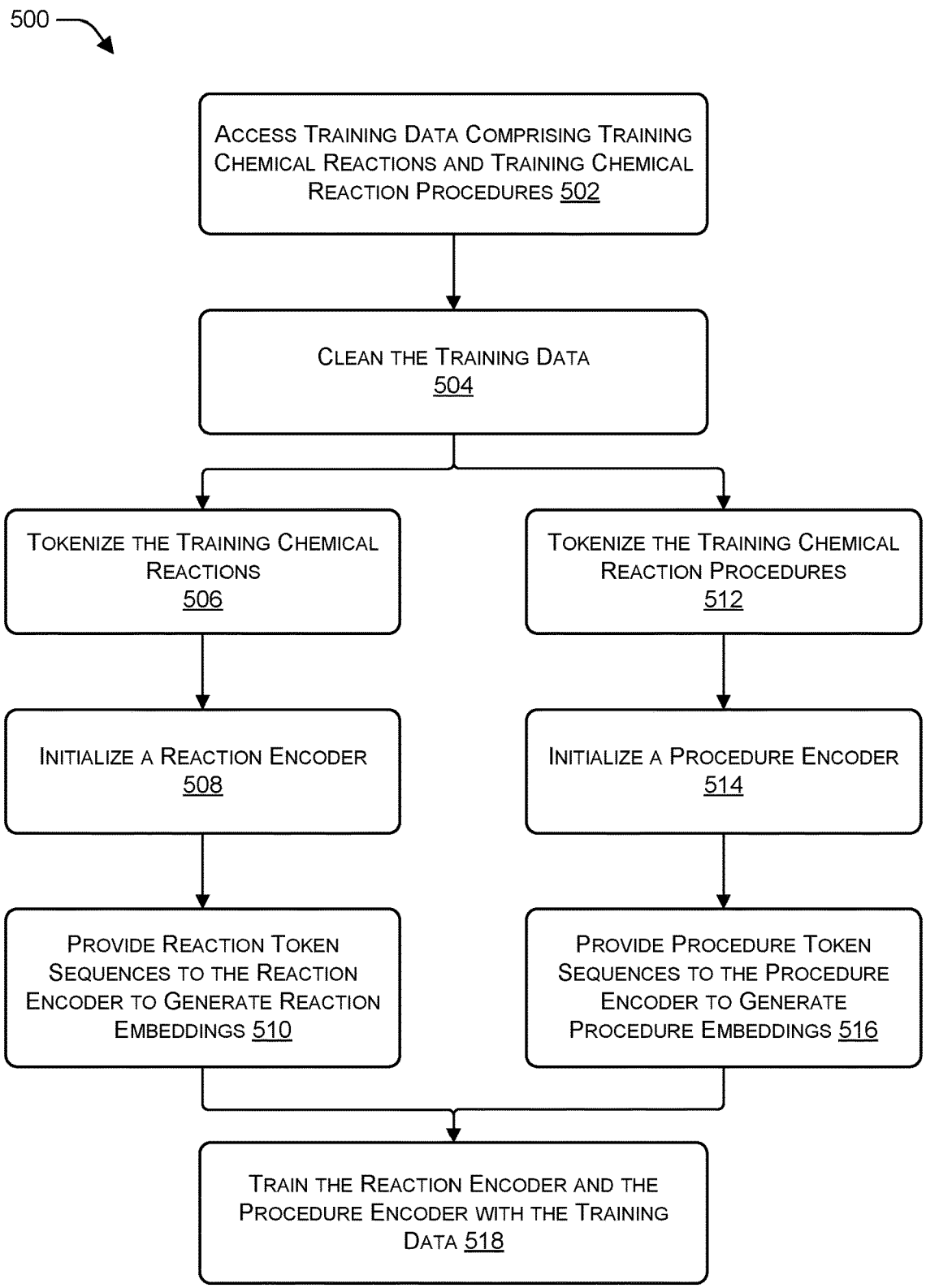
FIG. 5 is a flow diagram showing an illustrative process for training a reaction encoder and a procedure encoder to perform semantic matching between chemical reactions and chemical reaction procedures.

For ease of understanding, the processes discussed in FIGS. 4 and 5 are delineated as separate operations represented as independent blocks. However, these separately delineated operations should not be construed as necessarily order dependent in their performance. The order in which a process is described is not intended to be construed as a limitation, and any number of the described process blocks may be combined in any order to implement the process or an alternate process. Moreover, it is also possible that one or more of the provided operations is modified or omitted.

The particular implementation of the technologies disclosed herein is a matter of choice dependent on the performance and other requirements of a computing device. Accordingly, the logical operations described herein are referred to variously as states, operations, structural devices, acts, or modules. These states, operations, structural devices, acts, and modules can be implemented in hardware, software, firmware, special-purpose digital logic, and any combination thereof. It should be appreciated that more or fewer operations can be performed than shown in the figures and described herein. These operations can also be performed in a different order than those described herein.

It also should be understood that the illustrated methods can end at any time and need not be performed in their entirety. Some or all operations of the methods, and/or substantially equivalent operations, can be performed by execution of computer-readable instructions included on a computer-storage media, as defined below. The term "computer-readable instructions," and variants thereof, as used in the description and claims, is used expansively herein to include routines, applications, application modules, program modules, programs, components, data structures, algorithms, and the like. Computer-readable instructions can be implemented on various system configurations, including single-processor or multiprocessor systems, minicomputers, mainframe computers, personal computers, hand-held computing devices, microprocessor-based, programmable consumer electronics, combinations thereof, and the like.

Thus, it should be appreciated that the logical operations described herein are implemented (1) as a sequence of computer-implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as states, operations, structural devices, acts, or modules. These operations, structural devices, acts, and modules may be implemented in software, in firmware, in special purpose digital logic, and any combination thereof.

FIG. 4 shows a process 400 for outputting candidate chemical reaction procedures in response to a chemical reaction sketch. Process 400 may be implemented with any of the systems and architectures shown in FIGS. 1-3.

At operation 402, a chemical reaction sketch is received from a user computing device. The user computing device may be, for example, the user computing device 204 shown in FIG. 2. Chemical reaction sketch may be submitted in any format such as SMILES, IUPAC name, InChI, or chemical diagram. The chemical reaction sketch may include all or part of a chemical reaction. Thus, the chemical reaction sketch may include reactants and products, reactants only, products only, or even only a single chemical species from the chemical reaction. The chemical reaction sketch may be translated into a different format. For example, a chemical reaction sketch provided using IUPAC names may be translated or converted to a SMILES string.

At operation 404, the chemical reaction sketch is tokenized. Tokenization may be performed by a dedicated tokenizer. Tokenization is a way of separating a string of information into smaller units called tokens. It breaks components of the chemical entities (e.g., carbon backbones and functional groups) in the chemical reactions sketch into meaningful elements called tokens. The tokenizer breaks unstructured data and representations of chemical reactions into chunks of information that can be considered discrete elements. Tokenization creates a reaction token sequence.

At operation 406, a reaction embedding is generated by a reaction encoder. The reaction embedding may be a real-valued vector. The reaction encoder is one tower of a contrastive learning based two-tower model. The contrastive learning based two-tower model is trained by contrastive loss on labeled, pairwise training data. The training data includes training chemical reactions (e.g., SMILES strings) and training chemical reaction procedures (e.g., textual passages) for performing the training chemical reactions.

The reaction encoder may comprise any or all of a transformer network, a pooling layer, a normalization layer, and a neural network. The transformer network generates a transformer output from the reaction token sequence. In one implementation, the transformer network has six layers. The pooling layer generates a high-dimensional vector (e.g., 256 or 512 dimensions) from the transformer output. In one implementation, the pooling layer is a max pooler. The normalization layer generates a normalized vector from the high-dimensional vector. The neural network generates the reaction embedding from the normalized vector. In one implementation, the neural network has two layers.

At operation 408, similarity is determined between the reaction embedding and procedure embeddings generated by a procedure encoder of the contrastive learning based two-tower model. The procedure encoder is trained together with the reaction encoder. The procedure encoder may comprise any or all of a transformer network, a pooling layer, a normalization layer, and a neural network. The transformer network generates a transformer output from the reaction token sequence. In one implementation, the transformer network has six layers. The pooling layer generates a high-dimensional vector (e.g., 256 or 512 dimensions) from the transformer output. In one implementation, the pooling layer is a max pooler. The normalization layer generates a normalized vector from the high-dimensional vector. The neural network generates the reaction embedding from the normalized vector. In one implementation, the neural network has two layers.

The procedure embeddings are generated by the procedure encoder from chemical reaction procedures in a corpus of chemical reaction procedures. The corpus of chemical reaction procedures represents the datastore or knowledge base across which the search is performed. All or part of the corpus of chemical reaction procedures across which searches are performed may be used to train the model. In some implementations, a different set of chemical reaction procedures are used to train the model.

The reaction embedding from the query and the multiple procedure embeddings from the corpus of procedures are embedded in a shared embedding space. Due to the training, procedure embeddings that are most similar to the reaction embedding are closest to the reaction embedding in the shared embedding space. Thus, in one implementation, the similarity is determined by cosine similarity between vectors. Due to the tokenization of the inputs which include chemical entities, the similarity may identify a semantic similarity based on functional groups and carbon backbones structures.

At operation 410, the predetermined number of candidate chemical reaction procedures are output. The candidate chemical reaction procedures are those chemical reaction procedures from the corpus identified as being potentially a correct "match" or the right answer to the chemical reaction sketch provided as a query. The predetermined number may be any number such as, for example, from 1 to 20. In some implementations, the predetermined number may be specified by a user when making a query. The candidate chemical reaction procedures are those chemical reaction procedures from the corpus with procedure embeddings having a highest similarity to the reaction embedding. For example, if the predetermined number is five, then out of the chemical reaction procedures that are searched, the five with the highest similarity scores are identified and included in the output of candidate chemical reaction procedures.

FIG. 5 shows a process 500 for training a reaction encoder and a procedure encoder to perform semantic matching between chemical reactions and chemical reaction procedures. Process 500 may be implemented with any of the systems and architectures shown in FIGS. 2-3.

At operation 502, training data comprising labeled data pairs of training chemical reactions and training chemical procedures are accessed. The training data may be accessed from a training data store. Each of the label pairs of data includes the text of the chemical reaction procedure and a representation of the chemical reaction (e.g., a SMILES string) described in the text.

At operation 504, the training data is cleaned. The specific techniques for cleaning the training data may be varied and depend on the type of data. In one implementation, the training chemical reactions are cleaned by separating representations of chemical reactions into reactants and products. The training chemical reactions may also be cleaned by removing from the training data any representations of a chemical reaction that indicates the valence of an atom that exceeds the maximum allowed valence for that atom. For example, the maximum valence of carbon is 4; a chemical reaction that shows a carbon with more than four other atoms connected to it is assumed to have an error, and thus, will be removed. Removing one member of a labeled data pair also removes the other from the training data.

In some implementations, the format of the training chemical reactions is changed or translated into a different format. For example, a chemical reaction represented by a set of atom mappings may be converted into SMILES notation. If the conversion cannot be completed, that data pair may be removed from the training data. The training chemical reaction procedures may also be cleaned. For example, a training chemical reaction procedure, which is a textual passage, that begins with a lowercase letter or does not end with a period may be removed. Additionally, non-descriptive portions of the training chemical reaction procedure (e.g., passages that do not describe how to perform a chemical reaction) may be removed from the text.

Process 500 shows the initial steps of training for the reaction encoder and procedure encoder proceeding in parallel. Training of the reaction encoder is described initially below followed by training of the procedure encoder.

At operation 506, the training chemical reactions are tokenized. They may be tokenized by any suitable tokenizer. This creates reaction token sequences. Tokenization of the training chemical reactions may be performed in the same manner as tokenization of other chemical reactions described above.

At operation 508, the reaction encoder is initialized with weights developed from a different machine learning model. Initialization with relevant weights decreases the training time. In one implementation, the weights may come from a machine learning model that is configured to convert between the first representation and a second representation of a chemical entity (e.g., translate from SMILES to IUPAC names). However, the reaction encoder may also be trained without initialization or initialized with random weights.

At operation 510, the reaction token sequences are provided to the reaction encoder. The reaction encoder generates reaction embeddings from the reaction token sequences. The reaction embeddings are generated in a shared embedding space. The reaction embeddings are real-valued vectors.

The reaction encoder may include a reaction transformer network followed by a reaction pooling layer followed by a reaction normalization layer followed by a reaction neural network. The reaction transformer network may be implemented with a multi-head attention layer and a fully connected feed-forward layer. The reaction transformer network itself may contain multiple layers such as, for example, six layers and each of these layers itself contains a multi-head attention layer and at least one fully connected feed-forward layer. The reaction pooling layer may implement max pooling. In an implementation, the reaction neural network is a fully connected, feed-forward, multilayer neural network. For example, the reaction neural network may have two layers.

Turning now to training of the procedure encoder, at operation 512, the training chemical reaction procedures are tokenized. They may be tokenized by any suitable tokenizer.

This creates procedure token sequences. Tokenization of the training chemical reaction procedures may be performed in the same manner as tokenization of other chemical reaction procedures described above.

At operation 514, the procedure encoder is initialized with weights developed from a different machine learning model. Initialization with relevant weights decreases the training time. In one implementation, the weights come from a BERT-based language model of scientific publications (e.g., SciBERT). However, the procedure encoder may also be trained without initialization or with random initialization.

At operation 516, procedure token sequences are provided to the procedure encoder. The procedure encoder generates procedure embeddings from the procedure token sequences. The procedure embeddings are generated in the same shared embedding space as the reaction embeddings. The procedure embeddings may be real-valued vectors.

The procedure encoder may include a procedure transformer network followed by a procedure pooling layer followed by a procedure normalization layer followed by a procedure neural network. The procedure transformer network may be implemented with a multi-head attention layer and a fully connected feed-forward layer. The procedure transformer network itself may contain multiple layers such as, for example, six layers and each of these layers itself contains a multi-head attention layer and at least one fully connected feed-forward layer. The procedure pooling layer may implement max pooling. In an implementation, the procedure neural network is a fully connected, feed-forward, multilayer neural network. For example, the procedure neural network may have two layers.

At operation 518, the reaction encoder and procedure encoder are trained with the training data. The training is performed using back propagation to minimize the loss function between corresponding pairs of the reaction embeddings and the procedure embeddings. The loss function may be any suitable loss function used for training machine learning models such as InfoNCE.

EXAMPLES

The machine learning system of this disclosure was trained and tested to identify its ability to retrieve the correct chemical reaction procedure from a corpus of chemical reaction procedures when queried with a chemical reaction. In this example, each tower of the two-tower model included a transformer network with six layers. The transformer networks are based on the transformer described in Guo et al. The pooling layers are implemented as max poolers that take the maximum value for each dimension of the vectors output from the transformer network to create a single high-dimensional vector. This high-dimensional vector had either 256 or 512 dimensions. The normalization layers normalized the respective high-dimensional vectors by subtracting the mean and dividing by the standard deviation. The normalized vectors were provided to fully-connected feed-forward neural networks with two layers and ReLU connections. Each neural network output a real-valued vector in either 256 or 512 dimensions.

The machine learning system was trained using data pairs from the dataset Chemical reactions from US patents (1976-September 2016) as described in Lowe D., *Chemical reactions from US patents* (1976-September 2016). June 2017, doi:10.6084/m9.figshare.5104873.v1. This dataset includes chemical reactions extracted by text-mining from United States patents published between 1976 and September 2016 paired with the corresponding text describing the procedures for the chemical reactions. Each data pair includes a chemical reaction represented as a SMILES string, a textual passage describing a procedure for the chemical reaction, and a document identifier which is the patent number. The dataset includes 135,403 unique patent grants and 1,808,937 reaction-procedure pairs.

The training data was cleaned by separating the chemical reactions into reactants and products and canonicalizing the SMILES (represented as atom mapped) into canonical SMILES. The reactant side and the product side of the reactions are separated by the ">" symbol. Canonical SMILES of solvent or other reagents may be optionally inserted between the reactant and product side, separated by ">" symbol. Each reactant (resp. product) is separated from other reactants (resp. products) by the dot (".") symbol. Any chemical reaction that could not be canonicalized was discarded. All chemical reactions with an erroneous parse that indicated a valence for an atom which exceeds a maximum valance for the atom were also omitted. Duplicate chemical reactions with identical SMILES representations were also removed.

The text descriptions of the chemical reaction procedures were cleaned by removing non-descriptive text such as references to another portion of the document (e.g., "as shown above") or references to another document (e.g., "was processed as described previously in Jones et al."). Only text from the patents that provided details of a chemical reaction procedure was retained. Text passages of fewer than 20 words or greater than 250 words were also removed. Additionally, text passages that began with a lower-case letter or did not end with a period were removed. After cleaning the dataset 1,041,577 reaction-procedure pairs remained.

The dataset was split into training, development, and test data by year so that there were no document identifiers (i.e., patent numbers) or chemical reactions (i.e., SMILES strings) in common between the training, development, and test data. Data from patents issued from 1976-2013 were used for the training data; this provided 825,806 unique data pairs. Data from patents issued in 2014 were used for the development data; this provided 82,963 unique data pairs. Data from patents issued in 2015 and 2016 were used for the text data; this provided 132,808 unique data pairs.

The canonical SMILES strings were tokenized with a Byte-Pair Encoder (BPE) as described in Chithrananda, S. et al., *Large-scale self-supervised pretraining for molecular property prediction*. arXiv preprint arXiv:2010.09885, 2020. Start (<s>) and end (<\s>) tokens were added to the tokenized representations of the SMILES strings. Text of the chemical reaction procedures was tokenized using the techniques from SciBERT as described in Beltagy, I. et al.

The tower, or encoder, for the chemical reactions was initialized with weights from Guo et al. Although the model in Guo et al. was developed for converting from one molecular representation to another rather than for identifying relevant chemical reaction procedures, using it as a source of initial weights increased the speed of training relative to an uninitialized encoder. The second tower, or encoder, used with the chemical reaction procedures was initialized with the weights from distilled SciBERT which is a distillation that uses only the first six layers of SciBERT as described in Beltagy, I. et al.

The machine learning system was trained by backpropagation to minimize the InfoNCE loss between paired chemical reactions and chemical reaction procedures. The weights in the neural networks were developed by the backpropagation. This training maximizes the inner product (dot product) of the real-valued vector of a SMILES string with the real-valued vector of the corresponding chemical reaction procedure text.

Specifically, for the $i^{th}$ data point, let $z_i^{smiles}$ be the embedding of the chemical reaction represented in SMILES and $z_i^{text}$ be the embedding of the chemical reaction procedure text when passed through the respective encoders. Then the InfoNCE loss is constructed as follows:

correct chemical reaction procedure is included in the K retrieved results recall is scored as 1. If not recall is scored as 0. The average value for all samples in the search space is presented as the average recall at K. N represents the search space which is the number of chemical reaction procedures searched.

TABLE 1

Retrieval Performance.

| Run Parameters | Dev Metrics Avg. Recall@K = 2 | Test Search Space Size | Test Metrics - Avg. Recall@ | | |
|---|---|---|---|---|---|
| | | | K = 1 | K = 5 | K = 20 |
| Batch Size = 16, Seq. Length = 256 Learning rate = 1e−5 | 0.8666 | N = 10,000 N = 100,000 | 0.7937 0.7466 | 0.9517 0.9269 | 0.9855 0.9713 |
| Batch Size = 32, Seq. Length = 512, Learning rate = 1e−5 | 0.8777 | N = 10,000 N = 100,000 | 0.8021 0.7700 | 0.9564 0.9359 | 0.9847 0.9731 |
| Batch Size = 96, Seq. Length = 512, Learning rate = 5e−5 | 0.9073 | N = 10,000 N = 100,000 | 0.8352 0.8183 | 0.9664 0.9583 | 0.9900 0.9841 |
| Batch Size = 128, Seq. Length = 256, Learning rate = 1e−4 | 0.9108 | N = 10,000 N = 100,000 | 0.8367 0.8183 | 0.9710 0.9590 | 0.9901 0.9845 |

$$l_i^{smiles} = -\log\left(\frac{\exp(\langle z_i^{smiles}, z_i^{text}\rangle/\tau)}{\sum_j \exp(\langle z_i^{smiles}, z_j^{text}\rangle/\tau)}\right)$$

$$l_i^{text} = -\log\left(\frac{\exp(\langle z_i^{smiles}, z_i^{text}\rangle/\tau)}{\sum_j \exp(\langle z_i^{smiles}, z_i^{text}\rangle/\tau)}\right)$$

$$l_{smiles,text} = \frac{1}{|B|}\sum_k l_k^{smiles},$$

$$l_{text,smiles} = \frac{1}{|B|}\sum_{k'} l_{k'}^{text}$$

$$L = \alpha\, l_{SMILES,text} + (1-\alpha) l_{text,SMILES}$$

Training was performed for a maximum of 100 epochs on a GPU cluster with four Nvida® Tesla V100 GPUs with 16 GB of memory per GPU. The checkpoint with lowest validation error was saved. GPU batch sizes of 16, 32, 96, and 128 were tested. The maximum number of tokens uses to represent the chemical reactions and chemical reaction sequences (sequence length) was either 256 or 512. Longer token representations were truncated to the maximum length. A token length of 512 was found to describe almost all the chemical reaction procedures in the dataset without the need for truncation. A token length of 256 could describe over half the chemical reaction procedures without truncation. The initial learning rate was set to either 1e-5, 4e-5, or 5e-5 with linear decay and warmup of 10 k steps, and dropout probability of 0.2 for fully connected layers.

The trained model was tested with different combinations of run parameters of batch size, sequence length, and learning rate. The development data was used to develop the hyperparameters for the model. Given that the correct answer is known from the labeled test data (i.e., ground truth), average recall at K was calculated to identify if the matching chemical reaction procedure was in the top K results return when queried with a chemical reaction. If the The highest recall was achieved with a batch size of 128, a sequence length of 256, and a learning rate of 1e-4. Surprisingly, for K=5 (i.e., returning five candidate chemical reaction procedures) the correct procedure from a search space of 100,000 chemical reaction procedures was identified for 95.9% of the queries. This accuracy rate is much higher than has been achieved for other techniques used to search chemical texts.

Illustrative Computer Architecture

Figure 6:
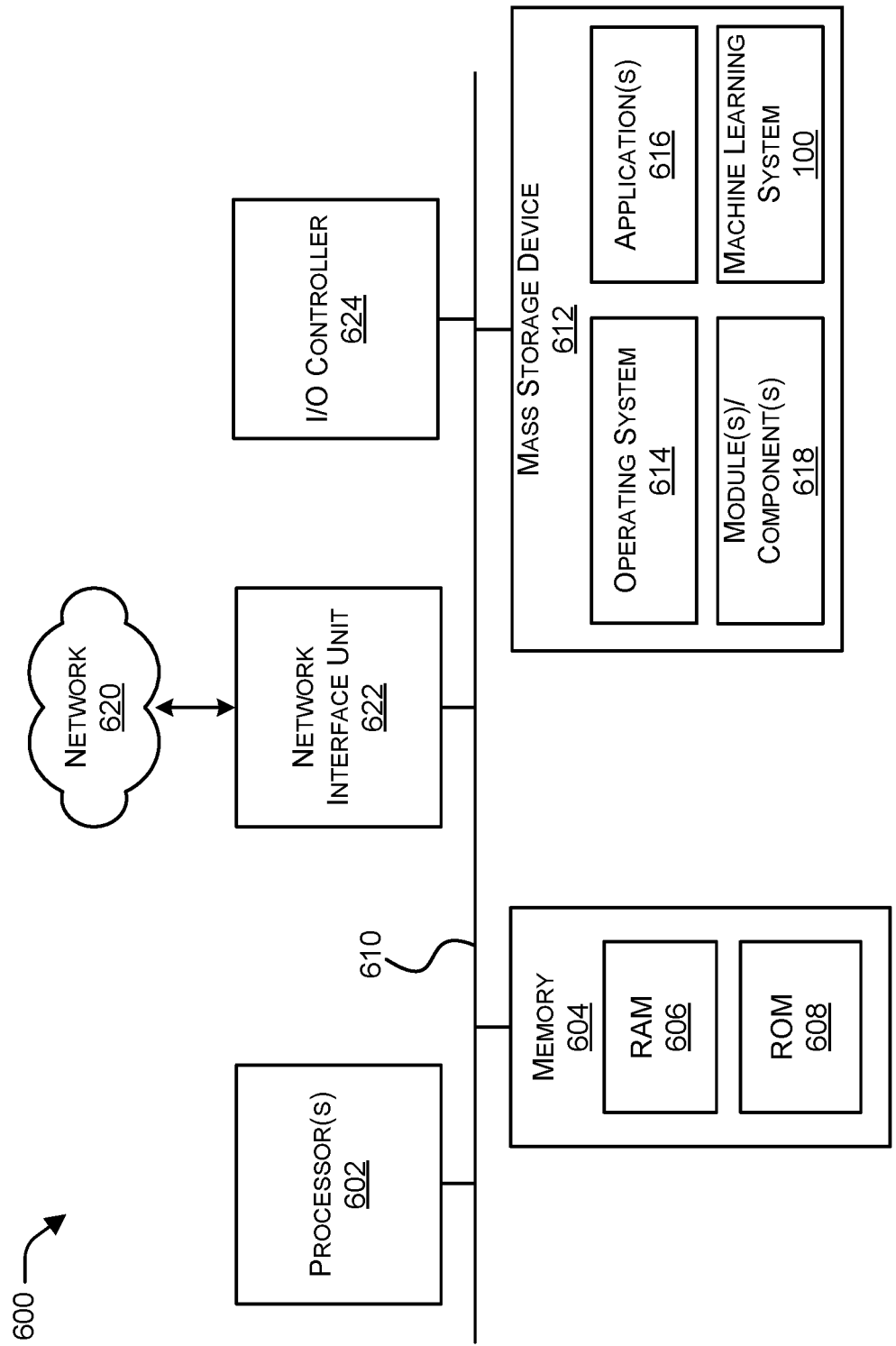
FIG. 6 is a computer architecture diagram illustrating an illustrative computer hardware and software architecture for a computing system capable of implementing aspects of the techniques and technologies presented herein.

FIG. 6 shows additional details of an example computer architecture 600 for a device, such as a computer or a server capable of executing computer instructions (e.g., a module or a component described herein). For example, computer architecture 600 may represent the user computing device 204 shown in FIG. 2. The computer architecture 600 illustrated in FIG. 6 includes one or more processor(s) 602, memory 604, including a random-access memory 606 ("RAM") and a read-only memory ("ROM") 608, and a system bus 610 that couples the memory 604 to the processor(s) 602. The processor(s) 602 may also comprise or be part of a processing system, processing unit, or hardware logic circuitry. In various examples, the processor(s) 602 of the processing system are distributed. Stated another way, one processor(s) 602 of the processing system may be located in a first location (e.g., a rack within a datacenter) while another processor(s) 602 of the processing system is located in a second location separate from the first location.

Processor(s) 602 can represent, for example, a CPU-type processing unit, a GPU-type processing unit, a field-programmable gate array (FPGA), another class of digital signal processor (DSP), or other hardware logic components that may, in some instances, be driven by a CPU. For example, illustrative types of hardware logic components that can be used include Application-Specific Integrated Circuits (ASICs), Application-Specific Standard Products (ASSPs), System-on-a-Chip Systems (SOCs), Complex Programmable Logic Devices (CPLDs), and the like.

A basic input/output system containing the basic routines that help to transfer information between elements within the computer architecture 600, such as during startup, is stored in the ROM 608. The computer architecture 600 further includes a mass storage device 612 for storing an operating system 614, application(s) 616, modules/components 618, the machine learning system 100, and other data described herein.

The mass storage device 612 is connected to a processor 602 through a mass storage controller connected to the bus 610. The mass storage device 612 and its associated computer-readable media provide non-volatile storage for the computer architecture 600. Although the description of computer-readable media contained herein refers to a mass storage device, it should be appreciated by those skilled in the art that computer-readable media can be any available computer-readable storage medium or communications medium that can be accessed by the computer architecture 600.

Computer-readable media can include computer-readable storage media and/or communication media. Computer-readable storage media can include one or more of volatile memory, nonvolatile memory, and/or other persistent and/or auxiliary computer storage media, removable and non-removable computer storage media implemented in any method or technology for storage of information such as computer-readable instructions, data structures, program modules, or other data. Thus, computer-readable storage media are tangible and/or physical forms of media included in a device and/or hardware component that is part of a device or external to a device, including RAM, static random-access memory (SRAM), dynamic random-access memory (DRAM), phase-change memory (PCM), ROM, erasable programmable read-only memory (EPROM), electrically erasable programmable read-only memory (EEPROM), flash memory, compact disc read-only memory (CD-ROM), digital versatile disks (DVDs), optical cards or other optical storage media, magnetic cassettes, magnetic tape, magnetic disk storage, magnetic cards or other magnetic storage devices or media, solid-state memory devices, storage arrays, network-attached storage, storage area networks, hosted computer storage or any other storage memory, storage device, and/or storage medium that can be used to store and maintain information for access by a computing device.

In contrast to computer-readable storage media, communication media can embody computer-readable instructions, data structures, program modules, or other data in a modulated data signal, such as a carrier wave, or other transmission mechanism. As defined herein, computer-readable storage medium does not include communication medium. That is, computer-readable storage media does not include communications media and thus excludes media consisting solely of a modulated data signal, a carrier wave, or a propagated signal, per se.

According to various configurations, the computer architecture 600 may operate in a networked environment using logical connections to remote computers through the network 620. The network 620 may be the same as the network 206. The computer architecture 600 may connect to the network 620 through a network interface unit 622 connected to the bus 610. An I/O controller 624 may also be connected to the bus 610 to control communication in input and output devices.

It should be appreciated that the software components described herein may, when loaded into the processor(s) 602 and executed, transform the processor(s) 602 and the overall computer architecture 600 from a general-purpose computing system into a special-purpose computing system customized to facilitate the functionality presented herein. The processor(s) 602 may be constructed from any number of transistors or other discrete circuit elements, which may individually or collectively assume any number of states. More specifically, the processor(s) 602 may operate as a finite-state machine, in response to executable instructions contained within the software modules disclosed herein. These computer-executable instructions may transform the processor(s) 602 by specifying how the processor(s) 602 transitions between states, thereby transforming the transistors or other discrete hardware elements constituting the processor(s) 602.

Figure 7:
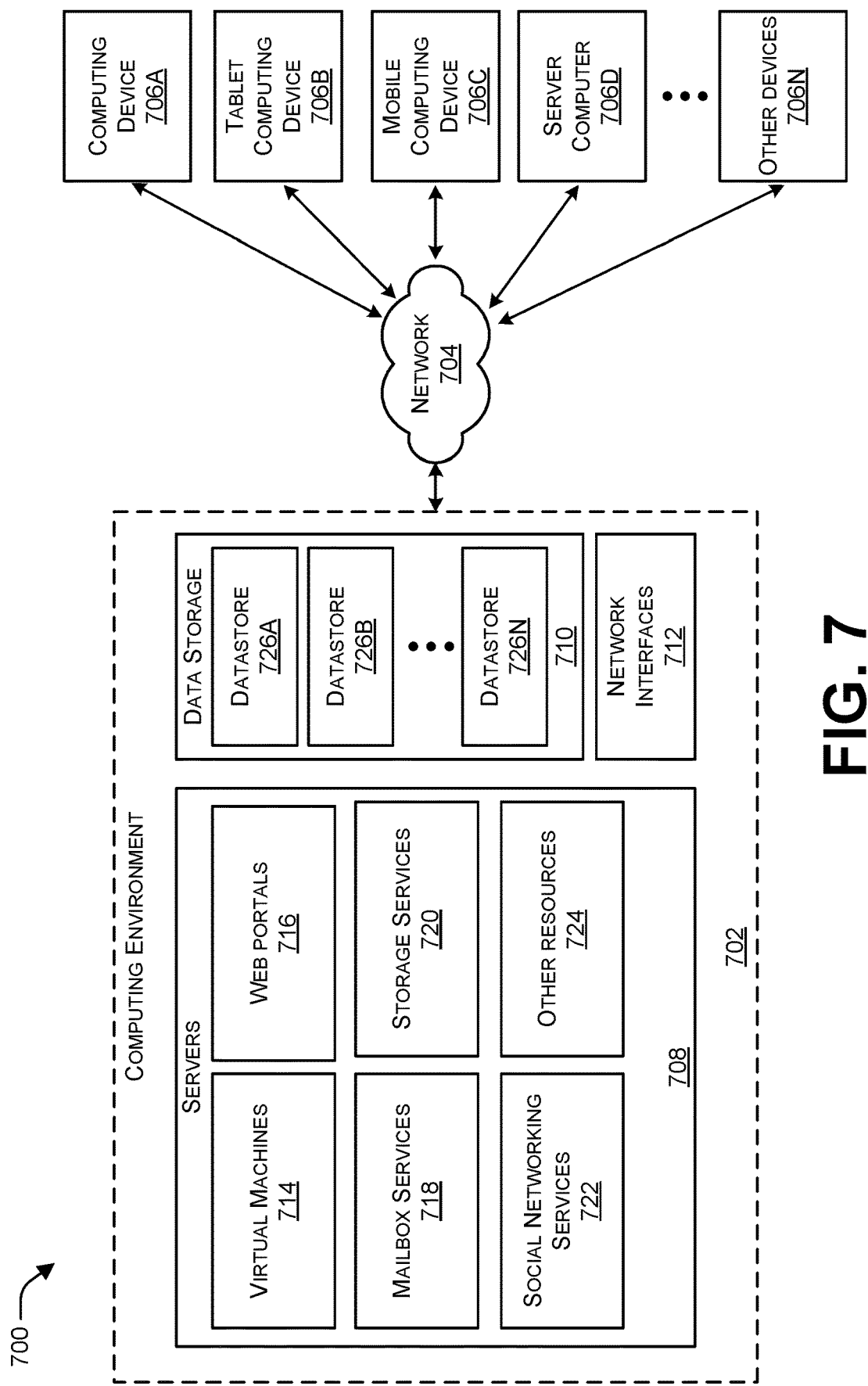
FIG. 7 is a diagram illustrating a distributed computing environment capable of implementing aspects of the techniques and technologies presented herein.

FIG. 7 depicts an illustrative distributed computing environment 700 capable of executing the components described herein. Thus, the distributed computing environment 700 illustrated in FIG. 7 can be utilized to execute any aspects of the components presented herein. Accordingly, the distributed computing environment 700 can include a computing environment 702 operating on, in communication with, or as part of the network 704. The network 704 may be the same as the network 206 shown in FIG. 2. The network 704 can include various access networks. One or more client devices 706A-706N (hereinafter referred to collectively and/or generically as "clients 706" and also referred to herein as computing devices 706) can communicate with the computing environment 702 via the network 704. In one illustrated configuration, the clients 706 include a computing device 706A such as a laptop computer, a desktop computer, or other computing device; a slate or tablet computing device ("tablet computing device") 706B; a mobile computing device 706C such as a mobile telephone, a smart phone, or other mobile computing device; a server computer 706D; and/or other devices 706N. The user computing device 204 shown in FIG. 2 is an example of a client 706. It should be understood that any number of clients 706 can communicate with the computing environment 702.

In various examples, the computing environment 702 includes servers 708, data storage 710, and one or more network interfaces 712. The servers 708 can host various services, virtual machines, portals, and/or other resources. In the illustrated configuration, the servers 708 host virtual machines 714, Web portals 716, mailbox services 718, storage services 720, and/or, social networking services 722. As shown in FIG. 7, the servers 708 also can host other services, applications, portals, and/or other resources 724. The other resources 724 may include the machine learning system 100 described above.

As mentioned above, the computing environment 702 can include the data storage 710. According to various implementations, the functionality of the data storage 710 is provided by one or more databases operating on, or in communication with, the network 704. The functionality of the data storage 710 also can be provided by one or more servers configured to host data for the computing environment 700. The data storage 710 can include, host, or provide one or more real or virtual datastores 726A-726N (hereinafter referred to collectively and/or generically as "datastores 726"). The datastores 726 are configured to host data used or created by the servers 708 and/or other data. That is, the datastores 726 also can host or store web page documents, word documents, presentation documents, data structures, algorithms for execution by a recommendation engine, and/or other data utilized by any application program. One or more of the datastores 726 may store the chemical reaction procedures 106 or the training data 222. Thus, datastore 218 and/or training datastore 224 of FIG. 2 may be included in the datastores 726. Aspects of the datastores 726 may be associated with a service for storing files.

The computing environment 702 can communicate with, or be accessed by, the network interfaces 712. The network interfaces 712 can include various types of network hardware and software for supporting communications between two or more computing devices including the computing devices and the servers. It should be appreciated that the network interfaces 712 also may be utilized to connect to other types of networks and/or computer systems.

It should be understood that the distributed computing environment 700 described herein can provide any aspects of the software elements described herein with any number of virtual computing resources and/or other distributed computing functionality that can be configured to execute any aspects of the software components disclosed herein. According to various implementations of the concepts and technologies disclosed herein, the distributed computing environment 700 provides the software functionality described herein as a service to the computing devices. It should be understood that the computing devices can include real or virtual machines including server computers, web servers, personal computers, mobile computing devices, smart phones, and/or other devices. As such, various configurations of the concepts and technologies disclosed herein enable any device configured to access the distributed computing environment 700 to utilize the functionality described herein for providing the techniques disclosed herein, among other aspects.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A machine learning system (100) for identifying one or more candidate chemical reaction procedures (102) from a chemical reaction sketch (104), the system comprising: a processor (602); a memory (604) comprising computer-readable instructions executable by the processor; a datastore (218) comprising a corpus of chemical reaction procedures (220); an interface (208) configured to receive the chemical reaction sketch from a user computing device (204); a reaction encoder (210) configured to create a reaction embedding (214) of the chemical reaction sketch, the reaction encoder comprising a reaction transformer network (302), a reaction pooling layer (304), a reaction normalization layer (306), and a reaction neural network (308); a procedure encoder (212) configured to create procedure embeddings (216) of the chemical reaction proce-dures in the corpus of chemical reaction procedures, the procedure encoder comprising a procedure transformer network (310), a procedure pooling layer (312), a procedure normalization layer (314), and a procedure neural network (316); a similarity-assessing mechanism (226) configured to determine a similarity between the reaction embedding and the procedure embeddings in a shared embedding space (322); and an output mechanism (228) configured to provide to the interface a predetermined number of candidate chemical reaction procedures from the corpus of chemical reaction procedures, the candidate chemical reaction procedures corresponding to procedure embeddings identified by the similarity-assessing mechanism as having the highest similarity to the reaction embedding.

Clause 2. The machine learning system of clause 1, wherein the reaction transformer network comprises multiple layers each including a multi-head attention layer and a fully-connected feed-forward layer configured to generate a reaction transformer output and the procedure transformer network comprises multiple layers each including a multi-head attention layer and a fully-connected feed-forward layer configured to generate a procedure transformer output.

Clause 3. The machine learning system of clause 2, wherein the reaction pooling layer generates a first high-dimensional vector from the reaction transformer output and the procedure pooling layer generates a second high-dimensional vector from the procedure transformer output.

Clause 4. The machine learning system of any of clauses 1 to 3, wherein the reaction normalization layer generates a first normalized vector from the first high-dimensional vector and the procedure normalization layer generates a second normalized vector from the second high-dimensional vector.

Clause 5. The machine learning system of any of clauses 1 to 4, wherein the reaction neural network and the procedure neural network are both fully connected, feed-forward, multilayer neural networks and the reaction neural network is configured to generate the reaction embedding from the first normalized vector and the procedure neural network is configured to generate the procedure embedding from the second normalized vector.

Clause 6. The machine learning system of any of clauses 1 to 5, wherein the reaction encoder and the procedure encoder are trained using contrasting learning on labeled pair-wise data of training chemical reaction procedures and training representations of chemical reactions, the training chemical reaction procedures provided to the procedure encoder and the training representations of chemical reactions provided to the reaction encoder.

Clause 7. A computer-implemented method of identifying one or more chemical reaction procedures (106) from a chemical reaction sketch (104) comprising: receiving from a user computing device (204) the chemical reaction sketch; tokenizing the chemical reaction sketch to create a reaction token sequence; generating a reaction embedding (214) from the reaction token sequence by a reaction encoder (210) of a contrastive learning based two-tower model, the contrastive learning based two-tower model trained by contrastive loss on training data (222) that includes training chemical reactions and training chemical reaction procedures for performing the training chemical reactions; determining similarity between the reaction embedding and procedure embeddings (216) in a shared embedding space (322), the procedure embeddings generated by a procedure encoder (212) of the contrastive learning based two-tower model from chemical reaction procedures (106) in a corpus of chemical reaction procedures (220); and outputting a predetermined number of candidate chemical reaction procedures (102) corresponding to procedure embeddings having a highest similarity to the reaction embedding.

Clause 8. The computer-implemented method of clause 7, wherein the chemical reaction sketch is a simplified molecular-input line-entry system (SMILES) representation of all or part of a chemical reaction.

Clause 9. The computer-implemented method of any of clauses 7 to 8, wherein the similarity is a semantic similarity based on functional groups and carbon backbone structures.

Clause 10. The computer-implemented method of any of clauses 7 to 9, wherein the reaction encoder comprises: a transformer network (302) that generates a transformer output from the reaction token sequence; a pooling layer (304) that generates a high-dimensional vector from the transformer output; a normalization layer (306) that generates a normalized vector from the high-dimensional vector; and a neural network (308) that generates the reaction embedding in the shared embedding space from the normalized vector.

Clause 11. The computer-implemented method of clause 10, wherein the transformer network has six layers, the pooling layer comprises a max pooler, the high-dimensional vector has 512 dimensions, and the neural network has two layers.

Clause 12. The computer-implemented method of any of clauses 7 to 11, wherein the procedure encoder comprises: a transformer network (310) that generates a transformer output from procedure token sequences that are tokenizations of the chemical reaction procedures; a pooling layer (312) that generates a high-dimensional vector from the transformer output; a normalization layer (314) that generates a normalized vector from the high-dimensional vector; and a neural network (316) that generates the procedure embeddings in the shared embedding space from the normalized vector.

Clause 13. The computer-implemented method of clause 12, wherein the transformer network has six layers, the pooling layer comprises a max pooler, the high-dimensional vector has 512 dimensions, and the neural network has two layers.

Clause 14. A computer-implemented method of training a machine learning system (100) for identifying chemical reaction procedures (106) from chemical reaction sketches (104) comprising: accessing training data (222) from a training datastore (224), the training data comprising labeled data pairs of training chemical reactions and training chemical reaction procedures for performing the chemical reactions; tokenizing the training chemical reactions from the training data to create reaction token sequences (318); providing the reaction token sequences to a reaction encoder (210) that generates reaction embeddings (214) in a shared embedding space (322); tokenizing the training chemical reaction procedures from the training data to create procedure token sequences (320); providing the procedure token sequences to a procedure encoder (212) that generates procedure embeddings (216) in the shared embedding space; and training the reaction encoder and the procedure encoder with the training data by backpropagation to minimize a loss function between corresponding pairs of the reaction embeddings and the procedure embeddings.

Clause 15. The computer-implemented method of clause 14, further comprising cleaning the training data by separating the training chemical reactions into reactants and products.

Clause 16. The computer-implemented method of any of clauses 14 to 15, further comprising cleaning the training data by removing any representations of a chemical reaction that indicates a valance of an atom that exceeds a maximum valance for the atom.

Clause 17. The computer-implemented method of any of clauses 14 to 16, wherein the reaction encoder comprises a reaction transformer network (302) followed by a reaction pooling layer (304) followed by a reaction normalization layer (306) followed by a reaction neural network (308) and the procedure encoder comprises a procedure transformer network (310) followed by a procedure pooling layer (312) followed by a procedure normalization layer (314) followed by a procedure neural network (316).

Clause 18. The computer-implemented method of clause 17, wherein the reaction transformer network and the procedure transformer network both comprise one or more layers where each layer comprises a multi-head attention layer and a fully-connected feed-forward layer.

Clause 19. The computer-implemented method of any of clauses 17 to 18, wherein the reaction neural network and the procedure neural network are both fully-connected, feed-forward, multilayer neural networks.

Clause 20. The computer-implemented method of any of clauses 14 to 19, further comprising initializing the reaction encoder with weights developed from a machine learning model configured to convert between a first representation of chemical entity and a second representation of chemical entity and initializing the procedure encoder with weights from a BERT-based language model of scientific publications.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications throughout this specification. Each of the cited references is individually incorporated herein by reference for its particular cited teachings as well as for all that it discloses.

The invention claimed is:

1. A machine learning system for identifying one or more candidate chemical reaction procedures from a chemical reaction sketch, the system comprising:
   a processor;
   a memory comprising computer-readable instructions executable by the processor;
   a datastore comprising a corpus of chemical reaction procedures;
   an interface configured to receive the chemical reaction sketch from a user computing device;
   a reaction encoder configured to create a reaction embedding of the chemical reaction sketch, the reaction encoder comprising a reaction transformer network, a reaction pooling layer, a reaction normalization layer, and a reaction neural network;
   a procedure encoder configured to create procedure embeddings of the chemical reaction procedures in the corpus of chemical reaction procedures, the procedure encoder comprising a procedure transformer network, a procedure pooling layer, a procedure normalization layer, and a procedure neural network;
   a similarity-assessing mechanism configured to determine a similarity between the reaction embedding and the procedure embeddings in a shared embedding space; and
   an output mechanism configured to provide to the interface a predetermined number of candidate chemical reaction procedures from the corpus of chemical reaction procedures, the candidate chemical reaction procedures corresponding to procedure embeddings identified by the similarity-assessing mechanism as having the highest similarity to the reaction embedding.

2. The machine learning system of claim 1, wherein the reaction transformer network comprises multiple layers each including a multi-head attention layer and a fully-connected feed-forward layer configured to generate a reaction transformer output and the procedure transformer network comprises multiple layers each including a multi-head attention layer and a fully-connected feed-forward layer configured to generate a procedure transformer output.

3. The machine learning system of claim 2, wherein the reaction pooling layer generates a first high-dimensional vector from the reaction transformer output and the procedure pooling layer generates a second high-dimensional vector from the procedure transformer output.

4. The machine learning system of claim 3, wherein the reaction normalization layer generates a first normalized vector from the first high-dimensional vector and the procedure normalization layer generates a second normalized vector from the second high-dimensional vector.

5. The machine learning system of claim 4, wherein the reaction neural network and the procedure neural network are both fully connected, feed-forward, multilayer neural networks and the reaction neural network is configured to generate the reaction embedding from the first normalized vector and the procedure neural network is configured to generate the procedure embedding from the second normalized vector.

6. The machine learning system of claim 1, wherein the reaction encoder and the procedure encoder are trained using contrasting learning on labeled pair-wise data of training chemical reaction procedures and training representations of chemical reactions, the training chemical reaction procedures provided to the procedure encoder and the training representations of chemical reactions provided to the reaction encoder.

7. A computer-implemented method of identifying one or more chemical reaction procedures from a chemical reaction sketch comprising:
   receiving from a user computing device the chemical reaction sketch;
   tokenizing the chemical reaction sketch to create a reaction token sequence;
   generating a reaction embedding from the reaction token sequence by a reaction encoder of a contrastive learning based two-tower model, the contrastive learning based two-tower model trained by contrastive loss on training data that includes training chemical reactions and training chemical reaction procedures for performing the training chemical reactions;
   determining similarity between the reaction embedding and procedure embeddings in a shared embedding space, the procedure embeddings generated by a procedure encoder of the contrastive learning based two-tower model from chemical reaction procedures in a corpus of chemical reaction procedures; and
   outputting a predetermined number of candidate chemical reaction procedures corresponding to procedure embeddings having a highest similarity to the reaction embedding.

8. The computer-implemented method of claim 7, wherein the chemical reaction sketch is a simplified molecular-input line-entry system (SMILES) representation of all or part of a chemical reaction.

9. The computer-implemented method of claim 7, wherein the similarity is a semantic similarity based on functional groups and carbon backbone structures.

10. The computer-implemented method of claim 7, wherein the reaction encoder comprises:
    a transformer network that generates a transformer output from the reaction token sequence;
    a pooling layer that generates a high-dimensional vector from the transformer output;
    a normalization layer that generates a normalized vector from the high-dimensional vector; and
    a neural network that generates the reaction embedding in the shared embedding space from the normalized vector.

11. The computer-implemented method of claim 10, wherein the transformer network has six layers, the pooling layer comprises a max pooler, the high-dimensional vector has 512 dimensions, and the neural network has two layers.

12. The computer-implemented method of claim 7, wherein the procedure encoder comprises:
    a transformer network that generates a transformer output from procedure token sequences that are tokenizations of the chemical reaction procedures;
    a pooling layer that generates a high-dimensional vector from the transformer output;
    a normalization layer that generates a normalized vector from the high-dimensional vector; and
    a neural network that generates the procedure embeddings in the shared embedding space from the normalized vector.

13. The computer-implemented method of claim 12, wherein the transformer network has six layers, the pooling layer comprises a max pooler, the high-dimensional vector has 512 dimensions, and the neural network has two layers.

14. A computer-implemented method of training a machine learning system for identifying chemical reaction procedures from chemical reaction sketches comprising:

accessing training data from a training datastore, the training data comprising labeled data pairs of training chemical reactions and training chemical reaction procedures for performing the chemical reactions;

tokenizing the training chemical reactions from the training data to create reaction token sequences;

providing the reaction token sequences to a reaction encoder that generates reaction embeddings in a shared embedding space;

tokenizing the training chemical reaction procedures from the training data to create procedure token sequences;

providing the procedure token sequences to a procedure encoder that generates procedure embeddings in the shared embedding space; and training the reaction encoder and the procedure encoder with the training data by backpropagation to minimize a loss function between corresponding pairs of the reaction embeddings and the procedure embeddings.

15. The computer-implemented method of claim 14, further comprising cleaning the training data by separating the training chemical reactions into reactants and products.

16. The computer-implemented method of claim 14, further comprising cleaning the training data by removing any representations of a chemical reaction that indicates a valance of an atom that exceeds a maximum valance for the atom.

17. The computer-implemented method of claim 14, wherein the reaction encoder comprises a reaction transformer network followed by a reaction pooling layer followed by a reaction normalization layer followed by a reaction neural network and the procedure encoder comprises a procedure transformer network followed by a procedure pooling layer followed by a procedure normalization layer followed by a procedure neural network.

18. The computer-implemented method of claim 17, wherein the reaction transformer network and the procedure transformer network both comprise one or more layers where each layer comprises a multi-head attention layer and a fully-connected feed-forward layer.

19. The computer-implemented method of claim 17, wherein the reaction neural network and the procedure neural network are both fully-connected, feed-forward, multilayer neural networks.

20. The computer-implemented method of claim 14, further comprising initializing the reaction encoder with weights developed from a machine learning model configured to convert between a first representation of chemical entity and a second representation of chemical entity and initializing the procedure encoder with weights from a BERT-based language model of scientific publications.

\* \* \* \* \*